United States Patent [19]

Goldstein

[11] Patent Number: 5,063,164
[45] Date of Patent: Nov. 5, 1991

[54] BIOMIMETIC SENSOR THAT SIMULATES HUMAN RESPONSE TO AIRBORNE TOXINS

[75] Inventor: Mark K. Goldstein, San Diego, Calif.

[73] Assignee: Quantum Group, Inc., San Diego, Calif.

[21] Appl. No.: 546,543

[22] Filed: Jun. 29, 1990

[51] Int. Cl.$^5$ .............................................. G01N 21/77
[52] U.S. Cl. ...................................... 436/169; 436/81; 436/120; 436/121; 436/134; 436/128; 422/58; 422/88; 422/91
[58] Field of Search ............................. 422/88, 91, 58; 436/120, 121, 134, 81, 902, 169, 128; 428/402.24; 252/315.2

[56] References Cited

U.S. PATENT DOCUMENTS

| | | | |
|---|---|---|---|
| 4,043,934 | 8/1977 | Shuler et al. | 252/186 |
| 4,439,488 | 3/1984 | Trimnell et al. | 428/402.24 |
| 4,482,635 | 11/1984 | Herskovitz et al. | 436/134 |
| 4,917,956 | 4/1990 | Rohrbach | 428/533 |

OTHER PUBLICATIONS

Windholz et al., *The Merck Index*, p. 229, #1630, 1983.
Shepherd, "Rapid Determination of Small Amounts of Carbon Monoxide," *Analytical Chem.*, Feb. 19, 1947.

*Primary Examiner*—Robert J. Warden
*Assistant Examiner*—Theresa A. Trembley
*Attorney, Agent, or Firm*—Christie, Parker & Hale

[57] ABSTRACT

The present invention relates to a biomimetic sensor for detecting the presence of airborne toxins, such as carbon monoxide, mercury, ethylene oxide, volatile organic materials, and hydrogen sulfide. The biomimetic sensor, which has a functional life of at least one year, comprises a porous, semi-transparent substrate into which is impregnated a self-regenerating chemical sensor reagent. The response of the biomimetic sensor mimics the human response to such toxins, with respect to sensitivity and affinity. The extended functional lifetime of the biomimetic sensor and the mimicking of the human response to the toxins are achieved by the use of a molecular encapsulant that encapsulates at least one component of the chemical sensor reagent.

24 Claims, No Drawings

BIOMIMETIC SENSOR THAT SIMULATES HUMAN RESPONSE TO AIRBORNE TOXINS

FIELD OF THE INVENTION

The present invention relates to an improved device for detecting the presence of a toxic gas or vapor by means of a solid-state chemical sensor system which has an extended functional life and which mimics the human response to these toxins. The extended functional life and mimicking of the human response are achieved through the use of molecular encapsulation of at least one component of the chemical sensor reagent. The biomimetic sensor is of particular use in detecting the presence of carbon monoxide, mercury, ethylene oxide, volatile organic material and hydrogen sulfide.

BACKGROUND OF THE INVENTION

Toxic, airborne contaminants, such as carbon monoxide, mercury, ethylene oxide, volatile organic materials and hydrogen sulfide, are often difficult to detect, since they may be colorless and odorless or they may be toxic at levels below which they can be seen or smelled by an average person. Also, in many environments, the smell of these gases may be masked by other odors that are present in the air. However, these airborne toxins present a growing danger to humans in, for example, automobiles, airplanes, industrial plants, mines, homes, and other environments in which humans are present for extended periods of time.

Numerous chemical detector tubes, for detecting the presence of toxins, have been in use for many years. For example, the use of palladium and molybdenum salts for carbon monoxide detection is described in *Analytical Chemistry*, Vol. 19, No. 2, pages 77–81 (1974). K. Shuler and G. Schrauzer improved upon this technology by adding a third metallic salt component which produces a self-regenerating catalyst that is short-lived. This catalyst, disclosed in U.S. Pat. No. 4,043,934, uses the impregnation of a carbon monoxide-sensitive chemical catalyst solution into powdered silica-gel substrates to give detectors sensitive-to-low concentrations of atmospheric carbon monoxide. While this system is effective in detecting carbon monoxide, it has not met with commercial acceptance due to the short functional life of the catalyst.

It is generally recognized that, for a carbon-monoxide sensor system to be commercially useful, it must have a functional life of at least one year. Tests have shown that the material described in U. S. Pat. No. 4,043,934 has a working life of only two to four months at room temperature and only three to four days at forty degrees Celsius.

Therefore, there is a need for a chemical sensor system capable of detecting the presence of airborne toxins, such as carbon monoxide, mercury, ethylene oxide, volatile organic materials and hydrogen sulfide, which has a functional life of at least one year. In addition, since these chemical sensor systems are designed to prevent injury to humans, it is important that the sensitivity of these sensor systems be similar to that of humans.

SUMMARY OF THE INVENTION

The present invention relates to a biomimetic sensor for detecting the presence of airborne toxins. The biomimetic sensor, which has a functional life of at least one year, comprises a porous, solid-state material which is sufficiently transmissive to light, to permit detection of the transmitted light by a light-emitting diode and photodiode or the like, and a self-regenerating chemical sensor reagent impregnated into the substrate. Upon exposure of the solid-state chemical sensor system to an airborne toxin, the chemical sensor reagent undergoes changes in its optical density. These changes in the optical density mimic the human response to the toxin, with respect to sensitivity and affinity. The major improvement, which results in the increased functional life of the chemical sensor system and the mimicking of the human response to these toxins, lies in the molecular encapsulation of at least one component of the chemical sensor reagent.

The present invention is useful for the detection of the presence of a variety of airborne toxins, such as carbon monoxide, mercury, ethylene oxide, volatile organic materials and hydrogen sulfide, which may be accumulated in the blood of a human.

DETAILED DESCRIPTION OF THE INVENTION

The present invention relates to an improved chemical sensor system for detecting the presence of airborne toxic gases or vapors (toxins). The chemical sensor system comprises a porous, semi-transparent substrate (i.e., the substrate is sufficiently transmissive to light to permit detection of the transmitted light by a photodiode, a light-emitting diode, or the like) and a self-regenerating chemical sensor reagent impregnated into the substrate.

The chemical sensor system undergoes a change in its optical density in response to contact with airborne toxins. Therefore, the presence of an airborne toxin can be quantitated by comparing the optical density of the chemical sensor reagent which has been exposed to a toxin, with the optical density of an unexposed chemical sensor system.

The change in the optical density of the chemical sensor system is dependent upon both the concentration of the toxin to which the chemical sensor system was exposed and the duration of the exposure. Therefore, the sensitivity of the chemical sensor system may be modified by extending the exposure time, when very low concentrations of the airborne toxins are present. In addition to the change in optical density on exposure to the toxins, the active chemical sensor system reacts selectively and reversibly with the toxin.

The chemical sensor system typically shows at least a fivefold drop in transmitted light (as detected by silicon-based photo detectors) under the following conditions: 200 ppm carbon monoxide, with the response observed in less than 2 hours; 400 ppm carbon monoxide, with the response observed in less than 30 minutes.

The porous, semi-transparent substrate, into which the chemical sensor system is impregnated, is selected from any of a number of commercially-available, porous, semi-transparent materials which are optically transmissive. Examples of such substrates include, but are not limited to, commercial silica-gel desiccants in bead form (available from most major suppliers of silica gel), porous silicon dioxide, and porous, leached, borosilicate glass such as VYCOR ("THIRSTY GLASS", Corning Glass Works, Corning, N.Y. Brand No. 7930). The porous glass may be obtained in plate, rod, or tubing form. Discs may be obtained by slicing the rods into suitable lengths. A variety of physical shapes and forms for the substrate may be obtained by suitable commercial processes.

The surface area is an important physical property of the porous, semi-transparent substrates, since surface area is proportional to the reactivity of the chemical sensor system. High surface areas are preferred to maximize the chemical sensor system that may be impregnated and to, therefore, optimize sensitivity. Chemical sensor systems made with porous silica discs and silica-gel beads remain viable for longer periods of time than sensors made with powdered silica-gel substrates. Small quantities of powdered silica-gel sensors exposed to the atmosphere have effective lifetimes ranging from only two weeks to four months, under laboratory and field conditions. Therefore, aerogels and xerogels are preferred as the substrate. Porous silicas such as VYCOR have a surface area of approximately 200 square meters/gram. Since this is a value typical of many powdered silica-gel substrates, the surface area of VYCOR is not believed to contribute to its observed enhanced lifetime properties.

The monolithic nature of the porous silica substrates also facilitate light transmission through the substrate. Porous silicas provide at least a tenfold increase in light transmission over powdered silica-gel sensors of comparable thickness. The increased light transmission permits the use of low-cost, conventional photo detectors, which do not display significant temperature dependence. Porous monolithic sensors are, therefore, more amenable to commercial applications than are powdered silica sensors.

The pore diameter of the porous, semi-transparent substrate is an important factor, since the pores must be able to accommodate the large molecular encapsulated complexes. Pore sizes of 200-to-1000 nm are preferred. Larger pores result in a loss of light transmissivity. Smaller pores are unable to accommodate the molecular encapsulant complexes.

The chemical sensor reagent used to impregnate the porous, semi-transparent substrate includes compounds such as those listed below. Preferably, the chemical sensor reagent is a mixture comprising at least one compound selected from each of the following groups:

Group 1: Soluble palladium salts such as palladium sulfate, palladium sulfite, palladium pyrosulfite, palladium chloride, palladium bromide, palladium iodide, palladium perchlorate, $CaPdCl_4$, $Na_2PdCl_4$ and $K_2PdCl_4$;

Group 2: Molybdenum and/or tungsten salts or acid salts such as silicomolybdic acid, salts of silicomolybdic acid, molybdenum trioxide, heteropolyacids of molybdenum, ammonium molybdate, alkali metal or alkaline earth metal salts of the molybdate anion or heteropolytugstenates;

Group 3: Copper salts such as copper sulfate, copper chloride, copper bromide, copper iodide, and copper perchlorate;

Group 4: Molecular encapsulants such as $\alpha$-cyclodextrin, $\beta$-cyclodextrin, modified $\beta$-cyclodextrin and $\gamma$-cyclodextrin, that have an internal cavity with a diameter of at least 50 nm; and Group 5: Soluble chloride salts such as lithium chloride, sodium chloride, lithium perchlorate, magnesium perchlorate, calcium perchlorate, aluminum perchlorate, platinum chloride, inorganic acids, calcium chloride, magnesium chloride, and cobalt chloride.

The improvement of the chemical sensor system comprises the inclusion of an encapsulating agent in the chemical sensor reagent. This results in encapsulation of at least one component of the chemical sensor reagent, which leads to an extension of the functional lifetime of the chemical sensor system, a mimicking of the human response to toxins, and reproducibility of the results obtained.

Mimicking of the response of humans to the toxic materials means that the chemical sensor system responds to the low concentrations of the toxins that are toxic to human beings, and that the system regenerates itself in a manner that is similar to the regeneration of biological systems. For example, in the case of carbon monoxide, hemoglobin has an affinity for carbon monoxide that is about 200 times greater than its affinity for oxygen. Therefore, carbon monoxide can readily displace oxygen on hemoglobin, making the hemoglobin unable to carry oxygen, or at least reducing the amount of oxygen that it is carrying. Therefore, the presence of very low concentrations of carbon monoxide is toxic to humans, and these low levels need to be detected by the chemical sensor system.

Additionally, the molecular encapsulant helps to control the regeneration response or the reversible reaction of the chemical sensor system (the biomimetic sensors) with toxins. Thus, in carbon-monoxide-free air, the chemical sensor system, which has carbon monoxide bound to the chemical sensor reagent, returns to its initial optical density at a rate similar to that for the dissociation of carbon monoxide from carboxyhemoglobin (hemoglobin that is bound to carbon monoxide in place of oxygen). The chemical sensor system, therefore, displays the desired self-regenerating properties for commercial biomimetic carbon-monoxide sensors.

The functional lifetime is also an important consideration for commercial chemical sensor systems, since the longer the lifetime, the less often the sensors have to be replaced, thus reducing the cost of the protection they afford. One year is considered to be the commercially-minimum requirement for most chemical sensor systems. Chemical sensor systems incorporating a molecular encapsulant not only meet but exceed this minimum commercial requirement. Additionally, the stabilizing effect of the molecular encapsulant overcomes the need for routine calibrations, an important consideration for consumer products, since these chemical sensor systems exhibit increased stability.

The encapsulating agents that are used are cyclodextrins, such as $\alpha$-cyclodextrin, $\beta$-cyclodextrin, modified $\beta$-cyclodextrin, and $\gamma$-cyclodextrin. Cyclodextrins are $\alpha$-(1→4) linked D-glucopyranose units. $\alpha$-cyclodextrin, $\beta$-cyclodextrin and $\gamma$-cyclodextrin are composed of 6, 7 or 8 units, respectively, linked together into a circular arrangement. As a result of the difference in the number of D-glucopyranose units internal diameter of the cyclodextrins also varies. $\alpha$-cyclodextrin has an internal diameter of about 57 nm, $\beta$-cyclodextrin has an internal diameter of about 78 nm, and $\gamma$-cyclodextrin has an internal diameter of about 95 nm. The modified $\beta$-cyclodextrin may be modified by the addition of such groups as fluorinated acetic acid, for example, heptakis (2,3,6,-tri-0-trifluoroaceto)-$\beta$-cyclodextrin. Modified $\beta$-cyclodextrins are preferred, since they have increased solubility when compared to unmodified cyclodextrin. Cyclodextrins are available from Sigma Chemical Co., St. Louis, Mo. (Catalog numbers C4642, C4767 and C4892).

In a preferred embodiment of the chemical sensor reagent, the Group 1 compound is palladium chloride, the Group 2 compound is silicomolydbic acid, the Group 3 compound is copper chloride, the Group 4 compound is a modified β-cyclodextrin, and the Group 5 compound is calcium chloride.

In another preferred embodiment, the chemical sensor reagent further includes an excess of halide ions, which are preferably chloride. It is particularly preferred that the halide compounds are non-volatile and that they remain soluble upon mixing with reagents from Groups 1, 2, 3, 4, and 5.

Studies have demonstrated that the aged carbon monoxide sensors, whether impregnated into silica gel, beads, or VYCOR, cannot be restored to functionality by addition of water once they fail. However, these same sensors have been restored, for short periods of time, by adding hydrogen chloride vapors. This implies that the retention of HCl is an important factor in extension of the lifetime of carbon monoxide sensors. The molecular encapsulant prefers HCl to water and may be useful for encapsulating HCl and for further extending the lifetime of the chemical sensor system.

Platinum chloride acts to "hold" HCl by forming complexes such as chloroplatinic acid ($H_2PtCl_6 \cdot 6H_2O$). However, in accelerated aging studies conducted at 60° C., the lifetime extension observed with conventional chemical sensor systems using such chemicals was only a factor of about two. In contrast, molecular encapsulated chemical sensor systems, with excess chloride, have lifetimes that are extended by a factor of 10 to 20.

Hygroscopic agents, such as calcium or lithium chloride, are useful in the chemical sensor system to prevent water loss. However, the addition of agents that could cause reduced solubility or precipitation are to be avoided. Preferred hygroscopic additives allow the use of higher concentrations of molecular encapsulants and inhibit precipitation. Additionally, calcium complexes with the $PdCl_4$ ion are believed to stabilize the $PdCl_4$ ion. Therefore, calcium ions are also preferred in certain formulations.

The non-volatile inorganic halides among Group 5 also extend the chemical sensor system lifetime by facilitating the retention of halide (chloride) ions in the system. Halide ions are also important in maintaining the self-regenerating nature of the chemical sensor system and allow reproducibility of the results obtained. The problem with simply using excess halide ions is that the excess halide ions also limit the carbon monoxide response and make it variable over time. Preferably, the non-volatile halide ions are present at a ratio of from about 2:1 to about 180:1 to the palladium ions.

Without wishing to be bound by scientific theory, it is believed that the observed enhancement of sensor lifetime is due to the capture of HCl and stabilization of palladium chloride, which is known to be unstable.

In another preferred embodiment of the present invention, the chemical sensor system includes absorbants and/or membranes to protect the chemical sensor system from external contaminants, such as aerosols, sprays, liquids, or plasticizers.

A typical procedure for preparing the chemical sensor system is as follows: The porous, semitransparent substrate is impregnated with the chemical sensor reagent by immersing the substrate in a bath which contains a mixture of at least one compound selected from each of the following groups:

Group 1: Palladium salts such as palladium sulfate, palladium sulfite, palladium pyrosulfite, palladium chloride, palladium bromide, palladium iodide, palladium perchlorate, $CaPdCl_4$, $Na_2PdCl_4$, and $K_2PdCl_4$;

Group 2: Molybdenum or tungsten salts such as silicomolybdic acid, salts of silicomolybdic acid, molybdenum trioxide, heteropolyacids of molybdenum, ammonium molybdate, alkali metal or alkaline earth salts of the molybdate anion or heteropolytungstenates;

Group 3: Copper salts such as copper sulfate, copper chloride, copper bromide, copper iodide, and copper perchlorate;

Group 4: Molecular encapsulants such as a α-cyclodextrin, β-cyclodextrin, modified β-cyclodextrin and γ-cyclodextrin that have an internal cavity with a diameter of at least 50 nm; and Group 5: Soluble chloride ions such as lithium chloride, sodium chloride, lithium perchlorate, magnesium perchlorate, calcium perchlorate, aluminum perchlorate, platinum chloride, inorganic acids, calcium chloride, magnesium chloride, and cobalt chloride.

It is preferred that the components in the chemical sensor reagent are present in the bath solution in the following ratio ranges:

Group 1:Group 2—0.01:1 to 0.5:1;
Group 3:Group 2—0.001:1 to 0.08:1;
Group 4:Group 2—1:1 to 20:1; and
Group 5:Group 2—0.01:1 to 10:1.

It is also preferred that the compound(s) selected from Group 5 is/are present in at least a stoichiometric amount compared to the compound selected from Group 3.

After the porous, semi-transparent substrate has been immersed in the bath, it is then removed and allowed to dry.

Various features and advantages of the chemical sensor system are illustrated in the following examples. It is to be understood that these examples merely illustrate the invention and are not intended to limit the scope of the invention, which is defined in the claims.

DESCRIPTION OF THE PREFERRED EMBODIMENTS

Biomimetic sensors were made by soaking pieces of porous VYCOR and silica-gel beads for several hours in the solutions described in each of the examples, to impregnate the VYCOR and silica-gel beads. The impregnated VYCOR and silica-gel beads were then air-dried. Measurements of the optical density of the prepared chemical sensor systems, after exposure to carbon monoxide, mercury ethylene oxide, volatile organic material, and hydrogen sulfide, were made using standard laboratory instruments.

EXAMPLE 1

Preparation of a Chemical Sensor System for the Detection of Carbon Monoxide Which Includes a Molecular Encapsulant Six porous VYCOR discs, having a diameter of approximately 6.4 mm and a thickness of 1.3 mm, were immersed in a chemical sensor reagent composed of:

0.25 ml palladium chloride (1% Pd in 1M HCl);
6.0 ml silicomolybdic acid (50 g/l);
4.4 ml copper chloride (10% w/v); and
one molar equivalent of β-cyclodextrin to palladium ions.

The changes in the optical density were determined by quantitating the amount of blue-green light transmitted through the substrate.

The prepared chemical sensor system discs were tested at 60° C. for one month and were compared to control discs that were prepared in a solution similar to that of the test discs, but which lacked the molecular encapsulant. The results showed that all of the discs prepared with the molecular encapsulant reacted with carbon monoxide in a manner similar to the response and binding of carbon monoxide to hemoglobin. The control discs, which lacked the molecular encapsulant, rapidly lost their ability to bind carbon monoxide.

Therefore, chemical sensor systems that incorporate a molecular encapsulant exhibit the sensitivity and reactivity required for the detection of airborne toxins in situations that would be required to warn humans of potential harmful exposure to the toxins.

EXAMPLE 2

Preparation of a Chemical Sensor System for the Detection of Carbon Monoxide Which Includes a Molecular Encapsulant Six porous VYCOR discs, having a diameter of approximately 6.4 mm and a thickness of 1.3 mm, were immersed in a chemical sensor reagent composed of:
  72 mg palladium chloride;
  10.0 ml silicomolybdic acid solution (50 g/l);
  1.0 ml copper chloride solution (10% w/w);
  one molar equivalent of modified $\beta$-cyclodextrin to palladium ions; and
  500 mg calcium chloride.

The changes in the optical density were determined by quantitating the amount of blue-green light transmitted through the substrate.

The prepared chemical sensor systems were exposed to ambient conditions for a period of time in excess of three years. These sensors retained their ability to respond to low levels of carbon monoxide in air in a manner that is similar to the response observed with the binding of carbon monoxide to human hemoglobin. The encapsulated samples have been regenerated for over 40 cycles and still react with carbon monoxide in a reproducible manner. The chemical sensor systems retain their reactivity, even after exposure to 40° C. to 60° C. for several months, and are capable of retaining their functional lifetime for up to 5 years.

Control samples which were prepared in accordance with the method given in Example 2, but which did not include a molecular encapsulant, rapidly lost their reactivity. Such control samples had lifetimes of less than 1 to 2 months at 60° C.

EXAMPLE 3

Detection of Mercury

Porous VYCOR discs, having a diameter of approximately 6.4 mm and a thickness of 1.3 mm, are immersed in a chemical sensor reagent composed of:
  90 mg palladium chloride;
  10.0 ml silicomolybdic acid solution (50 g/l);
  1.0 ml copper chloride solution (10% w/w);
  one molar equivalent of modified $\beta$-cyclodextrin to palladium ions; and
  250 mg calcium chloride.

The prepared chemical sensor system discs are then exposed to an airborne contamination containing mercury.

The changes in the optical density are determined by quantitating the amount of blue-green light transmitted through the substrate.

The change in the optical density of the solution is found to be proportional to the concentration of mercury present.

EXAMPLE 4

Detection of Hydrogen Sulfide

The method described in Example 1 is repeated. However, for the determination of hydrogen sulfide, the changes in the optical density are not determined by quantitating the amount of blue-green light transmitted through the substrate. Instead, since the chemical sensor reagent turns black, due to the precipitation of palladium ions, the overall reduction in transmitted light is determined.

EXAMPLE 5

Detection of Organic Materials

Porous VYCOR discs, having a diameter of approximately 6.4 mm and a thickness of 1.3 mm, are immersed in a chemical sensor reagent composed of:
  0.25 ml palladium chloride (1% Pd in 1M HCl);
  6.0 ml silicomolybdic acid (50 g/l);
  4.4 ml copper chloride (10% w/v); and
  one molar equivalent of $\beta$-cyclodextrin to palladium ions.

The gas containing the organic material is contacted with a silicon gel impregnated with a solution of chromic acid and potassium permanganate, which are present at a ratio of 1:1, and heated to 150° C. The chromic acid/potassium permanganate mixture is a strong oxidizing agent which oxidizes the organic materials to carbon monoxide. The carbon monoxide is then detected by the chemical sensor system.

EXAMPLE 6

Detection of Organic Materials

Porous VYCOR discs, having a diameter of approximately 6.4 mm and a thickness of 1.3 mm, are immersed in a chemical sensor reagent composed of:
  0.25 ml palladium chloride (1% Pd in 1M HCl);
  6.0 ml silicomolybdic acid (50 g/l);
  4.4 ml copper chloride (10% w/v); and
  one molar equivalent of $\beta$-cyclodextrin to palladium ions.

The chemical sensor system is exposed to an olefin, such as ethylene. The chemical sensor system is then heated to about 70° C. At this temperature the ethylene is converted to acetaldehyde, which is detected by the sensor as a change in the optical density of the chemical sensor reagent.

The present invention is described in relation to limited working embodiments and are for illustrative purposes. Variations will be apparent to those skilled in the art. Therefore, the present invention is not intended to be limited to the embodiments described above. The scope of the invention is defined by the following claims.

What is claimed is:

1. A biomimetic sensor for detecting the presence of airborne toxins comprising:
  a porous, semi-transparent substrate that is transmissive to light;
  means for detecting light transmitted through the substrate;
  a self-regenerating chemical sensor reagent for detecting airborne toxins, wherein the self-regenerating chemical sensor is able to regenerate itself for a period of at least one year at ambient conditions; and a molecular encapsulant encapsulating at least one component, but not all the components, of the chemical sensor reagent.

2. A biomimetic sensor as claimed in claim 1, wherein the substrate is selected from the group consisting of porous silica-gel beads, porous leached borosilicate glass, and porous silicon dioxide.

3. A biomimetic sensor as claimed in claim 2, wherein the porous, semi-transparent substrate has an pore size of about 200 nm to 1000 nm.

4. A biomimetic sensor as claimed in claim 1, wherein the chemical sensor reagent is a mixture in which at least one compound is selected from each of the following groups:

Group 1: Palladium salts selected from the group consisting of palladium sulfate, palladium sulfite, palladium pyrosulfite, palladium chloride, palladium bromide, palladium iodide, palladium perchlorate, $CaPdCl_4$, $Na_2PdCl_4$ and $K_2PdCl_4$;

Group 2: Molybdenum or tungsten salts selected from the group consisting of silicomolybdic acid, salts of silicomolybdic acid, molybdenum trioxide, heteropolyacids of molybdenum, ammonium molybdate, alkali metal or alkaline earth salts of the molybdate anion or heteropolytungstenates;

Group 3: Copper salts selected from the group consisting of copper sulfate, copper chloride, copper bromide, copper iodide, and copper perchlorate;

Group 4: Molecular encapsulants selected from the group consisting of a α-cyclodextrin, β-cyclodextrin, modified β-cyclodextrin and γ-cyclodextrin; and Group 5: Soluble chloride ions selected from the group consisting of lithium chloride, sodium chloride, lithium perchlorate, magnesium perchlorate, calcium perchlorate, aluminum perchlorate, platinum chloride, inorganic acids, calcium chloride, magnesium chloride, and cobalt chloride.

5. A biomimetic sensor as claimed in claim 4, wherein the molecular encapsulant has an internal cavity with a diameter of at least 50 nm.

6. A biomimetic sensor as claimed in claim 4, wherein the compounds from Groups 1, 2, 3, 4, and 5 are present in the following ratio ranges:
Group 1:Group 2—0.01:1 to 0.5:1;
Group 3:Group 2—0.001:1 to 0.08:1;
Group 4:Group 2—1:1 to 20:1; and
Group 5:Group 2—0.01:1 to 10:1.

7. A biomimetic sensor as claimed in claim 1, wherein the sensor reagent comprises means for detecting an airborne toxin selected from the group consisting of carbon monoxide, mercury, ethylene oxide, volatile organic material or hydrogen sulfide.

8. A biomimetic sensor as claimed in claim 4, wherein the compound from Group 1 is palladium chloride, the compound from Group 2 is silicomolybdic acid, the compound from Group 3 is copper chloride, the compound from Group 4 is a modified β-cyclodextrin, and the compound from Group 5 is calcium chloride.

9. A biomimetic sensor as claimed in claim 1, further comprising a hygroscopic agent selected from the group consisting of lithium chloride, sodium chloride, lithium sulfate, lithium perchlorate, calcium perchlorate, aluminum perchlorate, platinum chloride, an inorganic non-volatile acid, calcium chloride, cobalt chloride, and combinations thereof.

10. A biomimetic sensor as claimed in claim 9, wherein the biomimetic sensor includes a second hygroscopic agent selected from the group consisting of non-volatile halide ions at a ratio of 2:1 to 180:1 to the palladium ions.

11. A biomimetic sensor as claimed in claim 10, wherein the hygroscopic agent comprises a chloride ion.

12. A self-regenerating biomimetic chemical sensor system comprising:
a porous, semi-transparent substrate that is transmissive to light;
means for detecting the light transmitted through the substrate;
a self-regenerating chemical sensor reagent for detecting airborne toxins; and
means for extending the lifetime of the chemical sensor system, so that it will self-regenerate for at least one year at ambient conditions, by encapsulating at least one component, but not all the components, of the chemical sensor reagent in a molecular encapsulant.

13. A self-regenerating chemical sensor system as claimed in claim 12, wherein the molecular encapsulant is selected from the group consisting of α-cyclodextrin, β-cyclodextrin, modified β-cyclodextrin, γ-cyclodextrin, and combinations thereof.

14. A method of biomimetically detecting airborne toxins comprising:
immersing a porous, semi-transparent substrate in a chemical reagent system comprising at least one compound from each of the following groups:
Group 1: Palladium salts selected from the group consisting of palladium sulfate, palladium sulfite, palladium pyrosulfite, palladium chloride, palladium bromide, palladium iodide, palladium perchlorate, $CaPdCl_4$, $Na_2PdCl_4$ and $K_2PdCl_4$;
Group 2: Molybdenum or tungsten salts selected from the group consisting of silicomolybdic acid, salts of silicomolybdic acid, molybdenum trioxide, hetropolyacids of molybdenum, ammonium molybdate, alkali metal, or alkaline earth salts of the molybdate anion or heteropolytungstenates;
Group 3: Copper salts selected from the group consisting of copper sulfate, copper chloride, copper bromide, copper iodide, and copper perchlorate;
Group 4: Molecular encapsulants that encapsulate at least one but not all components of the chemical reagent system, selected from the group consisting of a α-cyclodextrin, β-cyclodextrin, modified β-cyclodextrin and γ-cyclodextrin; and
Group 5: Soluble chloride ions selected from the group consisting of lithium chloride, sodium chloride, lithium perchlorate, magnesium perchlorate, calcium perchlorate, aluminum perchlorate, platinum chloride, inorganic acids, calcium chloride, magnesium chloride and cobalt chloride;
drying the substrate impregnated with the chemical sensor reagent to form a chemical sensor system;
exposing the chemical sensor system to airborne toxins; and
evaluating the change in the optical density of the chemical sensor system for sensing airborne toxins.

15. A method as claimed in claim 14, wherein the molecular encapsulant has an internal cavity with a diameter of at least 50 nm.

16. A method as claimed in claim 14, wherein the porous, semi-transparent substrate has a pore size of 200 nm to 1000 nm.

17. A method as claimed in claim 14, wherein the compounds from Groups 1, 2, 3, 4, and 5 are present in the following ratio ranges:
   Group 1:Group 2—0.001:1 to 0.5:1;
   Group 3:Group 2—0.001:1 to 0.08:1;
   Group 4:Group 2—1:1 to 20:1; and
   Group 5:Group 2—0.01:1 to 10:1.

18. A method as claimed in claim 14, wherein the sensor reagent is exposed to an airborne toxin selected from the group consisting of carbon monoxide, mercury, ethylene oxide, volatile organic material or hydrogen sulfide.

19. A method as claimed in claim 14, wherein the compound from Group 1 is palladium chloride, the compound from Group 2 is silicomolybdic acid, the compound from Group 3 is copper chloride, the compound from Group 4 is a modified $\beta$-cyclodextrin, and the compound from Group 5 is calcium chloride.

20. A method as claimed in claim 14, further comprising a hygroscopic agent selected from the group consisting of lithium chloride, sodium chloride, lithium sulfate, lithium perchlorate, calcium perchlorate, aluminum perchlorate, platinum chloride, an inorganic non-volatile acid, calcium chloride, cobalt chloride, and combinations thereof.

21. A method as claimed in claim 20, wherein the method includes a second hygroscopic agent selected from the group consisting of non-volatile halide ions and is present at a ratio of 2:1 to 180:1 to the palladium ions.

22. A method as claimed in claim 21, wherein the hygroscopic agent comprises a chloride ion.

23. An improved biomimetic chemical sensor system having a chemical sensor reagent impregnated into a porous, semi-transparent substrate, the improvement comprising a molecular encapsulant that encapsulates at least one component but not all components of the chemical sensor reagent so that the chemical sensor system will self-regenerate for at least one year at ambient temperatures.

24. An improved chemical sensor system as claimed in claim 23, wherein the molecular encapsulant is selected from the group consisting of $\alpha$-cyclodextrin, $\beta$-cyclodextrin, modified $\beta$-cyclodextrin and $\gamma$-cyclodextrin.

* * * * *

UNITED STATES PATENT AND TRADEMARK OFFICE
CERTIFICATE OF CORRECTION

PATENT NO. : 5,063,164

DATED : November 5, 1991

INVENTOR(S) : Mark K. Goldstein

It is certified that error appears in the above-identified patent and that said Letters Patent is hereby corrected as shown below:

Column 4, line 54, after "units" insert -- linked together in each of the cyclodextrins, the --.

Column 10, line 44 change "hetropolyacids" to -- heteropolyacids --.

Column 11, line 10, change "0.001:1" to -- 0.01:1 --.

Signed and Sealed this

Twentieth Day of April, 1993

Attest:

MICHAEL K. KIRK

Attesting Officer

Acting Commissioner of Patents and Trademarks

UNITED STATES PATENT AND TRADEMARK OFFICE
CERTIFICATE OF CORRECTION

PATENT NO. : 5,063,164
DATED : November 5, 1991
INVENTOR(S) : Mark K. Goldstein

It is certified that error appears in the above-indentified patent and that said Letters Patent is hereby corrected as shown below:

```
Column 3, 35, change "200-to-1000 nm" to
         -- 2 nm to 10 nm --.
Column 3, line 61, change "50 nm" to -- 0.5 nm --.

Column 4, line 56, change "57 nm" to -- 0.57 nm --.
Column 4, line 57, change "78 nm" to -- 0.78 nm --.
Column 4, line 58, change "95 nm" to -- 0.95 nm --.

Column 6, line 14, change "50 nm" to -- 0.5 nm --.
Column 9, line 13, change "200 nm to 1000 nm" to
         -- 2 nm to 10 nm --.
Column 9, line 45, change "50 nm" to -- 0.5 nm --.

Column 11, line 3, change "50 nm" to -- 0.5 nm --
Column 11, lines 5,6, change "200 nm to 1000 nm" to
          -- 2 nm to 10 nm --.
```

Signed and Sealed this

First Day of November, 1994

Attest:

BRUCE LEHMAN

*Attesting Officer*     *Commissioner of Patents and Trademarks*